United States Patent [19]
Sammons et al.

[11] Patent Number: 5,906,724
[45] Date of Patent: May 25, 1999

[54] APPARATUS FOR SEPARATION OF NUCLEATED BLOOD CELLS FROM A BLOOD SAMPLE

[75] Inventors: David W. Sammons; Garland E. Twitty; Joseph G. Utermohlen, all of Tucson, Ariz.; Rizwan Sharnez, Sicklerville, N.J.

[73] Assignee: BioSeparations, Inc., Tucson, Ariz.

[21] Appl. No.: 08/899,283

[22] Filed: Jul. 23, 1997

Related U.S. Application Data

[62] Division of application No. 08/327,483, Oct. 21, 1994, Pat. No. 5,662,813.

[51] Int. Cl.$^6$ .................... G01N 27/26; G01N 27/447
[52] U.S. Cl. .................... 204/627; 204/450; 204/518; 204/543; 204/600; 204/630; 210/198.2; 210/209; 210/456
[58] Field of Search ............... 210/198.2, 209, 210/456; 204/450, 518, 543, 600, 627, 630; 422/101

[56] References Cited

U.S. PATENT DOCUMENTS

| | | | |
|---|---|---|---|
| 3,829,370 | 8/1974 | Bourat | 204/180.1 |
| 3,989,613 | 11/1976 | Gritzner | 204/301 |
| 4,185,964 | 1/1980 | Lancaster | 424/11 |
| 4,204,929 | 5/1980 | Bier | 204/301 |
| 4,323,439 | 4/1982 | O' Farrell | 204/180.1 |
| 4,362,612 | 12/1982 | Bier | 204/301 |
| 4,588,492 | 5/1986 | Bier | 204/301 |
| 4,673,483 | 6/1987 | Mandle | 204/301 |
| 4,925,572 | 5/1990 | Pall | 210/767 |
| 4,963,236 | 10/1990 | Rodkey et al. | 204/183.2 |
| 5,173,164 | 12/1992 | Egen et al. | 204/301 |
| 5,192,553 | 3/1993 | Boyse et al. | 424/529 |
| 5,275,933 | 1/1994 | Teng et al. | 435/2 |
| 5,336,387 | 8/1994 | Egen et al. | 204/301 |
| 5,432,054 | 7/1995 | Saunders et al. | 435/2 |

(List continued on next page.)

FOREIGN PATENT DOCUMENTS

| | | |
|---|---|---|
| WO90/06509 | 6/1990 | WIPO . |
| WO94/17209 | 8/1994 | WIPO . |
| WO94/25873 | 11/1994 | WIPO . |

OTHER PUBLICATIONS

Ivory, C.F. et al., Biotechnology Prog,. vol. 6, pp. 21–32, 1990.

Egen, N.B., Separation Science and Technology, vol. 22(5), pp. 1383–1403, 1987.

"Continuous Counteracting Chromatographic Electrophoresis" by Ivory, Cornelius F. and Gobie, William A., *Biotechnology Prog.*, vol. 6, pp. 21–32, (1990).

"Fluid Stabilization During Isoelectric Focusing in Cylindrical and Annular Columns" by Egen, N.B., Twitty, G.E., Thormann, W., and Bier, M., *Separation Science and Technology*, vol. 22(5), pp. 1383–1403, (1987).

"Isolation of fetal trophoblast cells from peripheral blood of pregnant women" by Mueler, et al. *Lancet*, vol. 336, pp. 197–200, (1990).

(List continued on next page.)

*Primary Examiner*—John Kim
*Attorney, Agent, or Firm*—David G. Rosenbaum; Sonnenschein, Nath and Rosenthal

[57] ABSTRACT

A charge-flow separation apparatus (CFS) for enriching rare cell populations, particularly fetal cells, from a whole blood sample by separating the rare cell fractions from whole fractions according to the relative-charge density and/or the relative binding affinity for a leukocyte depletion solid phase matrix is described. The apparatus having an internal cooling system allows for dissipating heat generated by the electric field of the apparatus. The internal cooling system, consisting of a plurality of cooling tubes to circulate coolant material, prevents cellular degradation typically associated with the high heat generated by the electric field and permits the use of a higher voltage gradient to shorten separation times.

6 Claims, 7 Drawing Sheets

U.S. PATENT DOCUMENTS

| | | | |
|---|---|---|---|
| 5,437,987 | 8/1995 | Tens et al. | 435/7.25 |
| 5,439,571 | 8/1995 | Sammons et al. | 204/180.1 |
| 5,457,024 | 10/1995 | Goldbard | 436/177 |
| 5,676,849 | 10/1997 | Sammons et al. | 210/806 |

OTHER PUBLICATIONS

"Isolating Fetal Cells From Maternal Blood, Advances in Prenatal Diagnosis Through Molecular Technology" by J.L. Simpson, M.D. and S. Elias, M.D., *JAMA*, vol. 270, pp. 2357–2361, (1993).

"Practical and Theoretical Implications of Fetal/Maternal Lymphocyte Transfer" by Walknowska, et al., *Lancet*, vol. 1, pp. 1119–1120, (1969).

"Filterability of Erythrocytes and Whole Blood in Preterm and Full–Term Neonates and Adults" by Linderkamp, et al. *Pediatric Research*, vol. 20, No. 12, pp. 1269–1273 (1986).

"Trophoblast Cells in Peripheral Blood From Pregnant Women", by Covone, et al., *Lancet*, vol. 2, pp. 841–843, (1984).

Isolating Fetal Erythroblasts From Maternal Blood with Identification of Fetal Trisomy by Fluorescent In Situ Hybridization (FISH) by Simpson, et al., *Prenatal Diag.*, vol. 12, S12 (Suppl.), (1992).

"Erythroid–Specific Antibodies Enhance Detection of Fetal Nucleated Erythrocytes in Maternal Blood", by D. Bianchi, et al., *Prenat Diagnosis*, vol. 13, pp. 293–300, (1993).

"Mid–Trimester Fetal Sex Determination from Maternal Peripheral Blood by Fluorescence In Situ Hybridization Without Enrichment of Fetal Cells" by H. Hamada, et al., *Prenatal Diagnosis*, vol. 15, pp. 78–81 (1995).

"Prenatal Diagnosis through the Analysis of Fetal Cells in the Maternal Circulation", by D. Bianchi, M.D. and Katherine Klinger, Ph.D., *Genetic Disorders and the Fetus*, pp. 759–770 (1992).

"Fetal cells in the blood of pregnant women: Detection and enrichment by fluorescence–activated cell sorting", by L. Herzenberg, et al., *Proc. Natl. Acad. Sci. USA*, vol. 76, No. 3, pp. 1453–1455, (Mar. 1979).

"Isolation of fetal DNA from nucleated erythrocytes in maternal blood" by D. Bianchi, et al., *Proc. Natl. Acad. Sci. USA*, vol. 87, No. 3, pp. 3279–3283, (May 1990).

"Fetal Cells in Maternal Blood: Prospects for Noninvasive Prenatal Diagnosis" by Joe Leigh Simpson and Sherman Elias, *Annals of the New York Academy of Sciences*, vol. 731 (Complete Book), pp. 1–270 (1994).

"Separation of pluripotent hematopoietic stem cells from spleen colony—forming cells" *Nature*, vol. 347, pp. 188–189 (Sep. 13, 1990).

"Circulation of CD34 Hematopoietic Stem Cells in the Peripheral Blood of High–Dose Cyclophosphamide–Treated Patients: Enhancement by Intravenous Recombinant Human Granulocyte–Macrophage Colony–Stimulating Factor", by S. Siena, et al., *Blood*, vol. 74, pp. 1905–1914 (Nov. 1989).

"Transplantation with Blood Stem Cells" by A. Zander, J. Lyding and S. Bielack, *Blood Cells*, vol. 17, pp. 301–309 (1991).

"Circulating Exteropoietic Precursors in Human Blood" by M. Ogawa and J. Sexton, *Clinical Research*, vol. 24, pp. 316A (1976).

"Characterization of an erythroid precursor cell of high proliferative capacity in normal human peripheral blood" by B. Clarke and D. Housman, *Proc. Natl. Acad. Sci. USA*, vol. 74, No. 3, pp. 1105–1109 (Mar. 1977).

"Purification and Characterization of Mouse Hematopoietic Stem Cells" by G. Spangrude, S. Heimfeld, I. Weissman, *Science*, vol. 241, pp. 58–62 (1988).

"Antigen CD34 Marrow Cells Engraft Lethally Irradiated Baboons" by R.J. Berenson, et al., *J. Clin. Invest.*, vol. 81, pp. 951–955, (1988).

Treatment of Aggressive Multiple Myeloma by High–Dose Chemotherapy and Total Body Irradiation Followed by Blood Stem Cells Autologous Graft by Jean–Paul Fermand, Yves Levy, Jean Gerota, March Benbunan, Jean Marc Cosset, Sylvia Cataigne, Maxime Siligmann and Jean–Claude Brouet, *Blood*, vol. 73, No. 1, pp. 20–23 (Jan. 1989).

"Normal Blood Cell Values in the Early Mid–Trimester Fetus" by D.S. Millar, L.R. Davis, C.H. Rodeck, K.H. Nicolaides and R.S. Mibashan, *Prenatal Diagnosis*, vol. 5, pp. 367–373 (1985).

"Human umbilical cord blood as a potential source of transplantable hematopoietic stem/progenitor cells" by H. Broxmeyer, G. Douglas, G. Hangoc, S. Cooper, J. Bark, D. English, M. Arny, L. Thomas and E. Boyse, *Proc. Natl. Acad. Sci. USA*, vol. 86, pp. 3828–3832 (May 1989).

"Enrichment of Erythrocytes of Fetal Origin From Adult–Fetal Blood Mixtures via Selective Hemolysis of Adult Blood Cells: An Aid to Antenatal Diagnosis of Hemoglobinopathies" by S. Boyer, A. Noyes and M. Boyer, *Blood*, The Journal of the American Society of Hematology, vol. 47, No. 6, pp. 883–897 (Jun. 1976).

"Carbonic anhydrases from human neonatal erythrocytes" by J. Sell and H. Peterixg, *J. Lab Clin Med*, vol. 84, pp. 369–377 (1974).

"Concentration of Fetal Red Blood Cells from a Mixture of Maternal and Fetal Blood by Anti–I of Hemoglobinopathies" by Y. W. Kan, D.G. Nathan, G. Cividalli, M.C. Crookston, *Blood*, vol. 43, No. 3, pp. 411–415, (Mar. 1974).

"Carbonic Anhydrase I is an Early Specific Marker of Normal Human Erythroid Differentiation" by J.L. Villeval, et al., *Blood*, vol. 66, No. 5, pp. 1162–1170, (Nov. 1985).

"Exploratory Studies on Detection of Hemoglobins in the Early Human Fetus In Utero" by V. Heading, et al., *Annals of the New York Academy of Sciences*, vol. 241, pp. 715–721 (1974).

"Immunological Basis for Detection of Sickle Cell Hemoglobin Phenotypes in Amniotic Fluid Erythrocytes" by S. Boyer, M. Boyer, A. Noyes and T. Belding, *Annals of the New York Academy of Sciences*, vol. 241, pp. 699–713, (1974).

"Colony Formation of Clone–Sorted Human Hematopoietic Progenitors" by H. Ema, T. Suda, Y. Mura, and H. Nakauchi, *Blood*, vol. 69, No. 3, pp. 953–956, (Mar. 1987).

"Developmental Haemopoiesis" by W.G. Wood, pp. 75–98.

"Blast Cell Colony Assay for Umbilical Cord Blood and Adult Bone Marrow Progenitors" by A. Leary and M. Ogawa, *Blood*, vol. 69, No. 3, pp. 953–956, (Mar. 1997).

"Fetal plasma erythropoietin concentration in red blood cell–isoimmunized pregnancies" by B. Thilaganthan, et al., *Am J Obstet Gynecol*, vol. 167, pp. 1292–1297, (Nov. 1992).

"The Role of M–CSF and GM–CSF in Fostering Placental Growth, Fetal Growth, and Fetal Survival" by T.G. Wegmann, et al., *Transplantation Proceedings*, vol. 21, No. 1, pp. 566–568, (Feb. 1989).

"Erythroblastosis and reticulocytosis in anemic fetuses" by K.H. Nicosides, et al., *Am J Obstet Gynecol*, vol. 21, No. 1, pp. 1063–1065, (Nov. 1989).

"SFL 23.6: A Monoclinal Antibody Reactive With CFU–E, Erythroblasts, and Erythrocytes" by A. Gupta, et al., *Blood*, vol. 66, No. 3, pp. 522–526, (1985).

"Erythroid Progenitors Forming Clusters In Vitro Demonstrate High Erythropoietin Sensitivity" by P. Lynn Ouellette and Frances C. Monette, *Journal of Cellular Physiology*, vol. 105, pp. 181–184, (1980).

"The Production of Myeloid Blood Cells and Their Regulation During Health and Disease" by Hal E. Broxmeyer and Douglas E. Williams, *Crit Rev Oncol Hemat*, vol. 8, No. 3, pp. 173–226, (1988).

"Rapid chromosome analysis with the use of spontaneously dividing cells derived from umbilical cord blood (fetal and neonatal)" by Robert E. Tipton, et al., *Amer. J. Obstet and Gynecol*, vol. 161, pp. 1546–1548, (1989).

"Isolation and Characterization of the CD34 Hematopoietic Progenitor Cells from the Peripheral Blood of Patients with Chronic Myeloid Leukemia" by F. Silvestri, et al., *International Journal of Cell Cloning*, vol. 9, pp. 474–490, (1980).

"Effects of Recombinant Human G–CSF, GM–CSF, IL–3, and IL–1α on the Growth of Purified Human Peripheral Blood Progenitors" by Y. Takaue, et al., *Blood*, vol. 76, No. 2, pp. 330–335, (Jul. 15, 1990).

"Physical Separation of Hemopoietic Stem Cells from Cell Forming Colonies in Culture" by R.G. Worton, et al., *Cell Physiol*, vol. 74. pp. 171–182, (1969).

"Stimulation of fetal hemoglobin synthesis in bone marrow cultures from adult individuals" by Th. Papayannopoulou, et al., *Proc. Natl. Acad. Sci. USA*, vol. 73, No. 6, pp. 2033–2037, (1976).

"Human Marrow Erythropoiesis in Culture: II. Heterogeneity in the Morphology, Time Course of Colony Formation, and Sedimentation Velocities of the Colony–Forming Cells" by Makio Ogawa, et al., *American Journal of Hematology*, vol. 3, pp. 29–26, (1977).

"'Pure' Human Hematopoietic Progenitors: Permissive Action of Basic Fibroblast Growth Factor" by M. Gabbianelli, et al., *Science*, vol. 249, pp. 1561–1564, (1990).

"Human Mononuclear Phagocyte Differentiation Antigens" by Al Dimitriu–Bona, et al., *The Journal of Immunology*, vol. 130, pp. 145–152, (1983).

"Flow Cytomeric Analysis of Human Bone Marrow: I. Normal Erythroid Development" by Michael R. Loken, et al., *Blood*, vol. 69, No. 1, pp. 255–23, (1987).

"Fetal cells in the maternal circulation: isolation by multiparameter flow cytometry and confirmation by polymerase chain reaction" by Stephen Wachtel, et al., *Human Reproduction*, vol. 6, No. 10, pp. 1466–1469, (1991).

"Expression of cell–surface HLA–DR, HLA–ABC and glycophorin during erythroid differentiation" by J. Robinson, et al., *Nature*, vol. 289, pp. 68–71, (1981).

"Isolation of human hematopoietic progenitor cells using monoclinal antibodies" by P.C.L. Beverley, et al., *Nature*, vol. 287, pp. 332–333, (1980).

"Changes in Cell Surface Antigen Expression During Hemopoietic Differentiation" by C. Sieff, et al., *Blood*, vol. 60, No. 3, pp. 703–713, (1982).

"Fetal nucleated cells in maternal peripheral blood: frequency and relationship to gestational age" by Hiromi Hamada, et al., *Human Genetics*, vol. 9, pp. 427–432 (1993).

"Monoclinal Antibodies Detecting Antigenic Determinants With Restricted Expression on Erythroid Cells: From the Erythroid Committed Progenitor Level to the Mature Erythroblast" by T. Yokochi, et al., *Blood*, vol. 63, No. 6, pp. 1376–1384, (Jun. 1984).

"Neonatal Hematology—Chapter 2: The Erythrocyte and its Disorders" by Frank A. Oski, *Hematology of Infancy and Childhood*, pp. 16–18, (1987).

"Adult Hemoglobin Synthesis by Reticulocytes from the Human Fetus at Midtrimester" by Morley D. Hellenberg, Michael M. Kaback, and Haig H. Kazazian, Jr., *Science*, vol. 174, pp. 698–702, (1971).

"Hemoglobins in Human Fetuses: Evidence for Adult Hemoglobin Production After the 11th Gestational Week" by Haris A. Pataryas and George Stamatoyannopoulos, *Blood*, vol. 39, pp. 688–696, (1972).

"Hemoglobin a Synthesis in the Developing Fetus" by Haig H. Kazazian, Jr. and Andrea P. Woodhead, *New England Journal of Medicine*, vol. 289, pp. 58–62, (1973).

"Analysis of Peripheral Maternal Blood Samples for the Presence of Placenta–Derived Cells Using Y–Specific Probes and McAb H315" by A. Covone, et al., *Prenatal Diagnosis*, vol. 8, pp. 591–607, (1988).

"Detection of Rare Cells at a Frequency of One Per Million by Flow Cytometry" by Hans–Joachim Gross, et al., *Cytometry*, vol. 14, pp. 519–526, (1993).

"Experimental test detects cancerous cells with record precision" *Arizona Daily Star*, Section A, p. 3, (1995).

"Model study detecting breast cancer cells in peripheral blood mononuclear cells at frequencies as low as $10^{-7}$" by Hans–Joachim Gross, et al., *Proc Natl. Acad. Sci. USA*, vol. 92, pp. 537–541, (1995).

"Isolation of fetal DNA from nucleated erythrocytes in maternal blood" by Diana W. Bianchi, et al., *Proc. Natl. Acad. Sci*, vol. 87, pp. 3279–3283, (1990).

"Detection and Isolation of Fetal Cells from Maternal Blood Using the Fluorescence–Activated Cell Sorter (FACS)" by G. Michael Iverson, et al., *Prenatal Diagnosis*, vol. 1, pp. 61–73 (1981).

"First trimester prental diagnosis of trisomy 21 in fetal cells from maternal blood" by S. Elias, et al., *The Lancet*, vol. 340, pp. 1033, (Oct. 24, 1982).

"Detection of fetal cells with 47,XY, +21 karyotype in maternal peripheral blood", by Diana W. Bianchi, et al., *Human Genetics*, vol. 90, pp. 368–370, (1992).

"Identifications and Comparison of CD34–Positive Cells and Their Subpopulations From Normal Peripheral Blood and Bone Marrow Using Multicolor Flow Cytometry" by James G. Bender, et al., *Blood*, vol. 77, pp. 2591–2596, (1991).

"Multiparameter–flow–cytometrical quantitation of circulating $CD34^+$– cells: correlation to the quantitation of circulating hemopoietic progenitor cells by in vitro colony–assay" by Stefan Serke, et al., *British Journal of Haematology*, vol. 77, pp. 453–459, (1991).

"Detection of aneuploidy in human interphase spermatozoa by fluorescence in situ hybridization (FISH)" by R.H. Martin, et al., *Cytogenet Cell, Genet*, vol. 64, pp. 23–26, (1993).

"Prenatal sex determination from maternal peripheral blood using the polymerase chain reaction" by Y.M. Dennis Lo, et al., *Human Genetics*, vol. 90, pp. 483, 488, (1993).

"Fetal Lymphocytes in the Maternal Blood" by Jim Schröder and Albert de la Chapelle, *Blood, The Journal of Hematology*, vol. 39, pp. 153–162, (1972).

"Fetal Leukocytes in the Maternal Circulation After Delivery" by Jim Schröder, Anja Thlikainen, and Albert de la Chapelle, *Transplantation*, vol. 17, pp. 346–354, (1974).

"Antenatal Sex Determination in Blood from Pregnant Women" by J.W. Siebers, et al., *Humangenetik*, vol. 28, pp. 273–280, (1975).

"Elimination of Malignant Clonogenic Breast Cancer Cells from Human Bone Marrow" by Ian C. Anderson, et al., *Cancer Research*, vol. 49, pp. 4659–4664, (1989).

"Prediction of Early Relapse in Patients with Operable Breast Cancer by Detection of Occult Bone Marrow Micrometastases" by Richard J. Cote, et al., *Journal of Clinical Oncology*, vol. 9, No. 10, pp. 1749–1756, (1991).

"Further Studies on the Antenatal Detection of Sickle Cell Anemia and Other Hemoglobinopathies" by Haig H. Kazazian, et al., *Hemoglobin and Red Cell Structure and Function*, pp. 337–345, (1972).

"Detection of the Sickle Gene in the Human Fetus" by Yuet Wai Kan, et al., *The New England Journal of Medicine*, vol. 287, pp. 1–5, (1972).

"Fluorescence In Situ Hybridization: A Sensitive Method for Trisomy 8 Detection in Bone Marrow Specimens" by Robert B. Jenkins, et al., *Blood*, vol. 79, pp. 3307–3315, (1992).

"Identification of Circulating Micromegakaryocytes in a Case of Refractory Anemia: An Electron Microscopic–Cytochemical Study" by J. Breton Gorius, et al., *Blood, The Journal of Hematology*, vol. 40, pp. 453–463, (1972).

"Cytogenetic Analysis in the Diagnosis of Acute Leukemia" by Sverre Heim, M.D., Ph.D., and Felix Mitelman, M.D., Ph.D., *Cancer*, vol. 70, pp. 1701–1709, (1992).

"Essential Haematology" by A.V. Hoffbrand and J.E. Pettit, *Blackwell Scientific Publication*, Third Edition, pp. 1–424 (1993).

"Fetal and Neonatal Haematology" by I.M. Hann, B.E.S. Gibson and E.A. Letsky (Complete Book), (1991).

"Fluorescence in situ Hybridization on Enriched Nucleated Erythrocytes from Newborn Cord Blood" by P.N. Rao, M.J. Pettenati, W. Stewart, A. Sheikh, N. Bui, K. Yokobata, and C. Gaiser, *Cytogenetics Laboratory article*, pp. 142–143.

"Prenatal Diagnosis of Fetal Hemoglobin Lepore–Boston Disease on Maternal Peripheral Blood" by C. Camaschella, A. Alfarano, E. Gottardi, M. Travi, P. Primignani, F. Caligaris Cappio, and G. Saglio, *Blood*, vol. 75, pp. 2102–2106, (1990).

"Identification of Specific Hemoglobins Within Individual Erythrocytes" by V. Headings, et al., *Blood*, vol. 45, No. 2, pp. 263–271, (Feb. 1975).

"Differential activity of recombinant colony–stimulating factors in supporting proleferation of human peripheral blood and bone marrow myeloid progenitors in culture" by D. Caracciolo, S. Clark and G. Rovera, *British Journal of Haematology*, vol. 72, pp. 306–311, (1989).

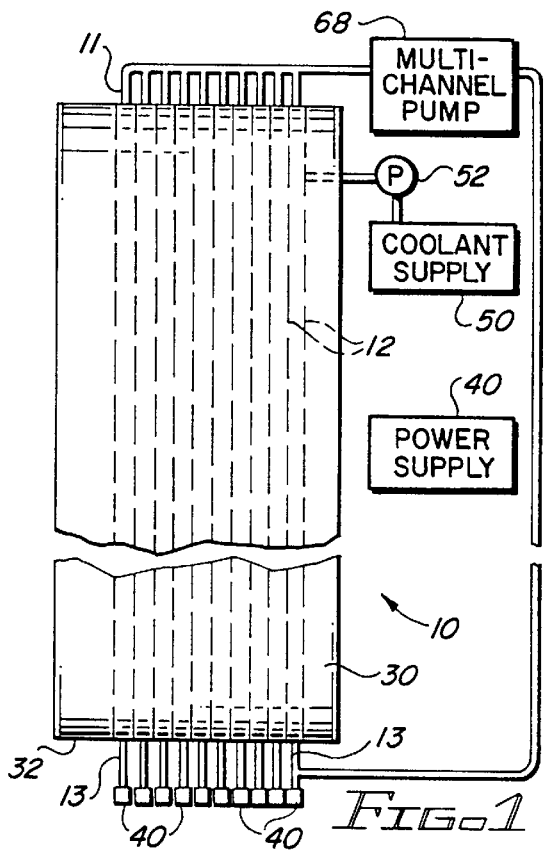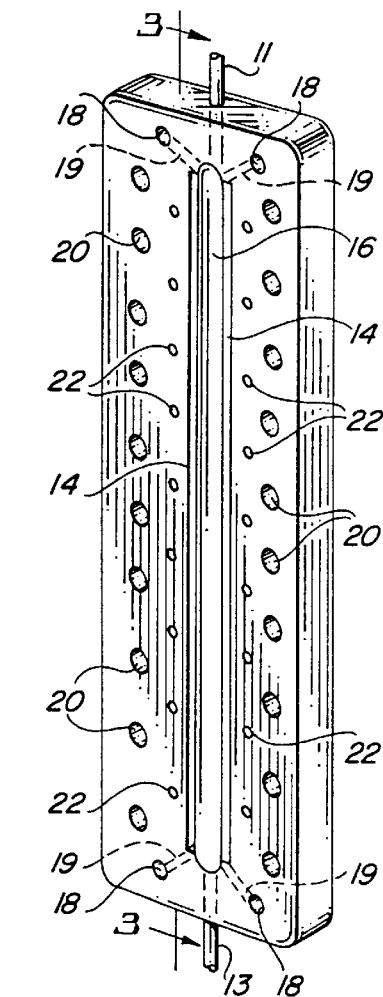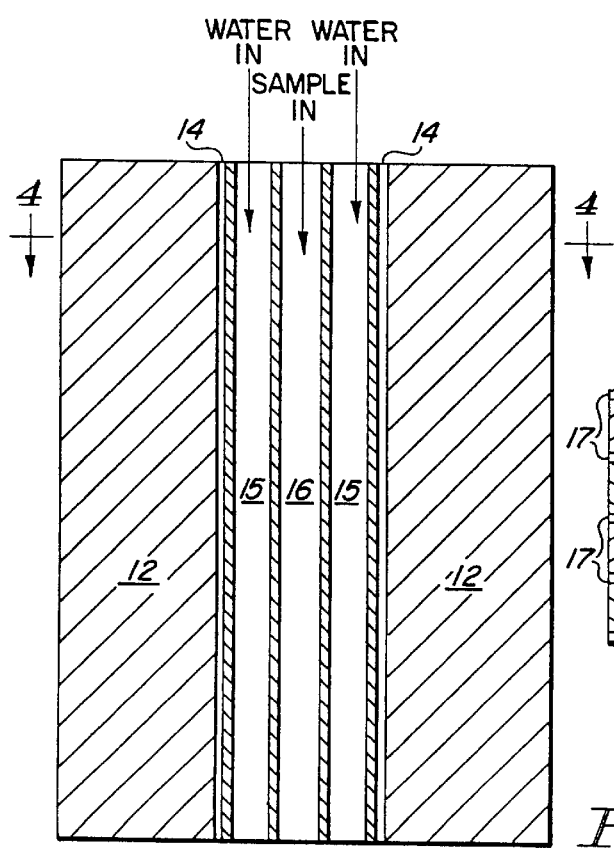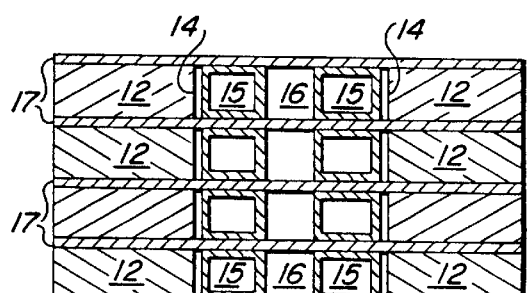

APPARATUS FOR SEPARATION OF NUCLEATED BLOOD CELLS FROM A BLOOD SAMPLE

This application is a division of application Ser. No. 08/327,483 filed Oct. 21, 1994 which application is now U.S. Pat. No. 5,662,813.

BACKGROUND OF THE INVENTION

The present invention relates generally to separation offetal erythrocytes from maternal blood samples. More particularly, the present invention provides a system and non-invasive method for enriching the population of nucleated fetal erythrocytes or nucleated fetal red blood cells ("NRBCs") obtained from maternal blood samples by separating the NRBCs from the mother's erythrocytes, leukocytes and other blood components. More specifically, the present invention offers a system and method for enriching the population of NRBCs from a maternal blood sample which concentrates the NRBCs by electrophoresis and/or adsorption-filtration or affinity filtration.

Physicians have long sought to develop non-invasive methods for prenatal diagnosis because the available methods, amniocentesis and chorionic villus sampling (CVS) are potentially harmful to the mother and to the fetus. The rate of miscarriage for pregnant women undergoing amniocentesis is increased by 0.5–1%, and that figure is slightly higher for CVS. Because of the inherent risks posed by amniocentesis and CVS, these procedures are offered primarily to older women, i.e., those over 35 years of age, who have a statistically greater probability of bearing children with congenital defects.

Some non-invasive methods have already been developed to diagnose specific congenital defects. For example, maternal serum alpha-fetoprotein, and levels of unconjugated estriol and human chorionic gonadotropin can be used to identify a proportion of fetuses with Downs syndrome. Similarly, ultrasonography is used to determine congenital defects involving neural tube defects and limb abnormalities.

Separation of nucleated fetal erythrocytes from maternal blood has been proposed as a viable method for facilitating prenatal diagnosis of genetic disorders. Fetal NRBCs have been separated from maternal blood by flow cytometry using a lysing reagent (European Published Patent Application No. 582736, published Feb. 16, 1994); by triple gradient discontinuous gradient gel electrophoresis (Bhat, et al, U.S. Pat. No. 5,275,933, issued Jan. 4, 1994); by separation from nucleated cells using leukocyte depletion and lysis of non-nucleated erythrocytes using ammonium chloride (Goldbard, PCT Publication WO 9417209, published Aug. 4, 1994); by use of anti-CD71 monoclonal antibody and magnetic beads and in-situ fluorescence hybridization (FISH) (Ahlert, et al, German Published patent application No. 4222573, published Aug. 12, 1993) or by other antibodies specific to a fetal erythrocyte antigen (Bianchi, PCT Publication Wo 9107660, published May 30, 1991).

SUMMARY OF THE INVENTION

The present invention demonstrates that fetal nucleated red blood cells exhibit consistent migration patterns in an electric field according to surface charge density which are different and distinct from the migration patterns of adult enucleated red blood cells. By using a novel charge-flow separation (CFS) method, described hereinafter, the present invention is able to divide maternal blood into fractions according to the surface charge density characteristics of each cell type. As the blood cells in a maternal blood sample move through the CFS apparatus, they are focused into compartments by opposing forces, namely buffer counter-flow and electric field, and then are directed into waiting collection tubes. An apparatus and method of counterflow focusing suitable for use with the system and method of the charge-flow separation of the present invention are disclosed in our U.S. Pat. Nos. 5,336,387 and 5,173,164, which are hereby incorporated by reference. A preferred embodiment of a CFS apparatus and method will be described in greater detail hereinafter.

The inventive CFS system and method has been successfully used to recover nucleated red blood cells from the peripheral circulation of pregnant women. The recovered NRBCs were identified histologically. The NRBCs exhibited consistent migration patterns whether they came from maternal blood or from umbilical cord blood collected at birth. No NRBCs were found in blood from nulliparous women.

Because the inventive system and method of charge-flow separation of NRBCs from maternal blood is based on the intrinsic physical properties of the NRBCs, there is little need for extensive preparation of the maternal blood sample. The cells may be processed at greater than or equal to 60,000 cells per second and specialized training is not required. When the inventive charge-flow separation system and method is used, the recovered cells are viable, thus raising the possibility of further enrichment by cell culture.

In conjunction with or in addition to the charge-flow separation system and method, the present invention also includes an affinity separation method for separating NRBCs from other cell populations in a maternal blood sample. The adsorption-filtration affinity method of the present invention entails layering a maternal blood sample onto a fibrous adsorption-filtration filter medium having a nominal pore size of about 8 microns and being capable of 40–80% leukocyte immobilization, with a 70–80% post-wash leukocyte retention rate, and which is extremely hydrophilic, being capable of wetting with solutions having surface tensions of up to 85–90 dynes, which has a hold up volume of 40–70 $\mu l/cm^2$ for a single layer of adsorption-filtration filter medium and which is characterized by low to medium protein binding. The preferred adsorption-filtration separation filter medium is that sold by Pall Corporation under the trademarks "LEUKOSORB" TYPES A and B or that described in U.S. Pat. Nos. 4,923,620, 4,925,572, or European Patent No. 313348, each of which is hereby incorporated by reference.

The charge-flow separation system and method and the adsorption-filtration separation system and method of the present invention may be used separately or may be used in conjunction with one another to achieve enrichment of the nucleated fetal red blood cell population in a maternal blood sample.

BRIEF DESCRIPTION OF THE FIGURES

FIG. 1 is a diagrammatic view of a first embodiment of the charge-flow separation apparatus according to the present invention.

FIG. 2 is a perspective view of a separation cell according to the present invention.

FIG. 3 is a cross-sectional view taken along line 3—3 of FIG. 2.

FIG. 4 is a cross-sectional view illustrating multiple adjacent separation cells according to the present invention.

DESCRIPTION OF PREFERRED EMBODIMENTS

FIRST EMBODIMENT

Charge-flow Separator

Figure 5:
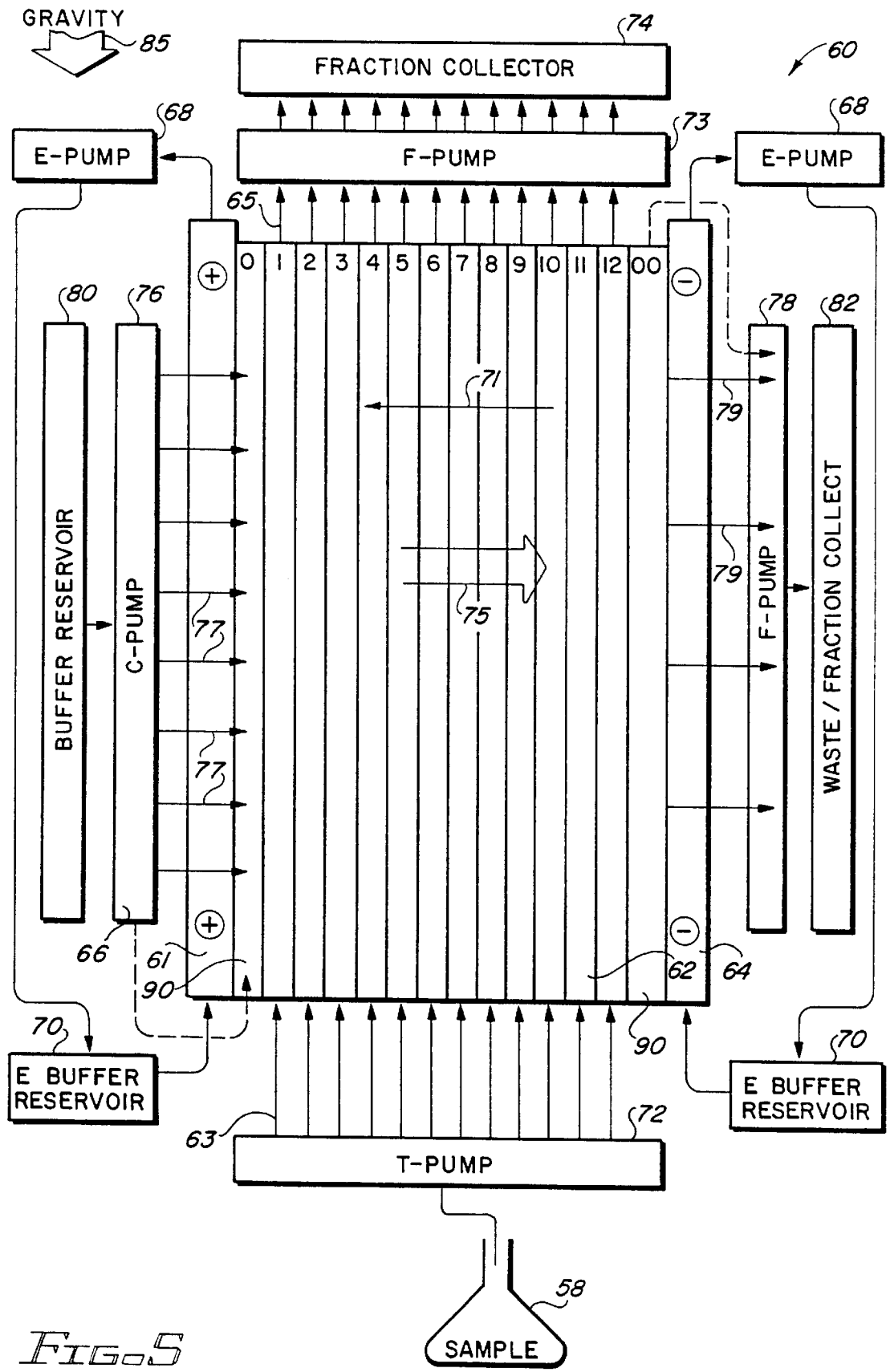
FIG. 5 is a diagrammatic view of a second embodiment of the charge-flow separation apparatus according to the present invention.

Turning to the accompanying Figures, and with particular reference to FIGS. 1–4, there is shown a multi-compartment charge-flow separator 10 according to a preferred embodiment of the present invention. The charge-flow separator is comprised of an array of subcompartments 12 with two electrode compartments 30, 32 on either end of the array. All subcompartments 12 for this electrophoretic separation cell are identical. Each subcompartment 12 consists generally of a planar body which has a narrow channel 16 formed within the planar body. Channel 16 acts as the separation chamber for processing the sample. The subcompartments 12 are adjacently arrayed in a co-planar fashion. Membranes 17 are interdisposed between the individual subcompartments 12. Membranes 17 which serve as delimiting inter-subcompartmental boundaries for the narrow channel 16 and effectively separate each adjacent channel 16 into discrete separation chambers. Each subcompartment 12 is provided with a linear array of openings 20 which receive a bolt or other fastening means to clamp together the array of aligned subcompartments 12. Each subcompartment also is provided with a linear array of alignment openings 22, which receive alignment pins to maintain a uniform width of the channel 16 along its longitudinal aspect. The array is bolted or clamped together, whereby the electrode compartments function as end-plates which provide a rigid structural support. With the electrode compartments 30, 32 provided on either end of the array, an electrical field applied to the electrophoretic separator runs perpendicular to the planar aspect of subcompartments 23 and the membranes 17. Appropriate electrolytes are pumped into their respective electrode compartments. Continuous recycling of the electrolytes removes electrolytic gases.

The membranes 17 reduce inter-subcompartmental fluid convection and mixing of the separated sample zones. A parallel array of membranes 17, oriented perpendicular to the separation axis, confines fluid convection to the individual subcompartments 12. The parallel array of membranes 17 benefit the separation process while preventing detrimental fluid convection between subcompartments 12.

Each subcompartment 12 is provided with a heat exchanger 14 to dissipate Joule heat generated during the electrophoretic separation. The heat exchanger 14 is disposed in the channel 16 of each subcompartment 12 such that at least a substantial portion of the longitudinal inner walls of channel 16 formed by the planar body 12, are associated with heat exchanger 14. According to the preferred embodiment of the invention, heat exchanger 14 comprises either a quadrilateral or circular cross-sectional tubing having a depth or diameter corresponding to the thickness of the planar body 12. The heat exchanger 14 connects to inlet and outlet ports 18 at the ends of the length of the cavity. Inlet and outlet ports 18 are preferably formed by providing co-axially aligned inlet and outlet ports 18 in adjacent arrayed subcompartments 12, each port 18 having fluid conduit 19 between the port 18 and the heat exchanger 14. Fluid conduit 19 may be integral with heat exchanger 14 or a discrete component.

Sample inlet 11 and collection 13 ports are also provided at each end of channel 16 and are in fluid flow communication therewith. Both inlet port 11 and collection port 13 are connected to a multichannel pump 60 which pumps the sample solution into channels 16 of individual subcompartments 12 and concurrently removes separated solution from the collection ports 13.

The volume of the electrophoretic separator according to the present invention is determined by the number of subcompartments 12 and the length of channel 16 in each subcompartment 12.

According to the best mode contemplated for the invention, each subcompartment 12 is preferably 0.1 to 0.4 cm in thickness, and may be die cut, extruded, molded or otherwise formed as may be known in the art. Regardless of the length of channel 16 or number of subcompartments 12, the thickness of the each subcompartment 12, and, hence, channel 16, i.e., the distance between two membranes 17, should be about 0.1 to about 0.4 cm. Further, an effective dimension of the channel 16 which forms the separation chamber, should be about 50 cm in length, 0.2 cm in width and 0.3 cm in thickness, which yields an effective total volume of 3 ml within channel 16.

Because of its dielectric properties, a silicone rubber material is well suited for sample containment in an electrophoretic separator, however, other electrically insulating materials are also effective. Because of its elastic properties, silicone rubber, together with the membranes 17, acts as a gasket between adjacent subcompartments 12 when the subcompartment array (FIG. 1) is bolted or clamped together.

The membranes used in the embodiment of the present invention are preferably woven polytetrafluoroetylene, polyvinylidone fluoride (FVDP), cellulose, nitrocellulose, polycarbonate, polysulfone, microporous glass or ceramics, or woven monofilament nylon screens. The screens may be formed of a woven filament, or may be microporous non-woven materials, or solid matrices with opening formed by sacrificial sites imparted by irradiation by laser or other energy sources such as gamma irradiation.

The electrode compartments 30, 32, provided at each end of the subcompartment array, provide a cavity for a platinum electrode. The electrode compartments 30, 32 are constructed from a suitable plastic material, preferably acrylic, and serve as a rigid end plate allowing the subcompartment array to be bolted together. In order to remove electrolytic gases from the electrolytic cavity, they are equipped with inlet and exit ports for the flow-through operation of the electrolytes. The electrolytes may be recirculated within each compartment 30 or 32, may be flowed through each compartment 30, 32 in a single pass or the anolyte may be mixed with the catholyte.

To facilitate assembly of the apparatus 10, the subcompartments 12, and the electrode compartments 30, 32, have a plurality of openings perpendicular to their flat faces. Bolts are inserted into the openings, which form one long bore hole upon the co-axial alignment of the components, which tightened to seal the subcompartments and electrode compartments against leakage. Additionally, a plurality of alignment openings 22 are provided in the planar bodies 12 and adjacent to or in close proximity to the channel 16. The alignment openings 22 serve to maintain uniform longitudinal alignment of channel 16, by engagement upon alignment pins (not shown).

Sample inlet 11 and collection 13 ports may be disposed within the silicone rubber material and pass from each end of the channel 16 and extend external to the planar body of the subcompartment 12. Each of the sample inlet 11 and collection 13 ports are connected to the multichannel pump 60.

Continuous-flow processing requires the provision of means for dissipating the Joule heat generated by the applied electric field. The apparatus of the present invention has the heat exchange means 14 for the recirculation of a coolant either attached to, or made as an integral part of the planar body of each subcompartment 12 such that the heat exchange means 14 forms side walls of channel 16. The heat exchange means 14 according to the preferred embodiment of the invention, consists of cooling tubes 14 having the same cross-sectional diameter or depth as that of the channel 16. Except as hereinafter described otherwise, each subcompartment 12 has associated with it a parallel pair of cooling tubes 14, each of which has inlet and exit ports 18 provided at the ends of the longitudinal axis of the subcompartment 12. The inlet and outlet ports 18 of all subcompartments 12 open into the same feed lines running perpendicular to the planar aspect of each subcompartment 12 through the array. The feed lines on either end of the silicone rubber spacer are formed by openings perpendicular to the planar aspect of the planar body of each subcompartment 12 and are in fluid flow communication upon bolting or clamping of the subcompartment array. The coolant is supplied from a coolant supply 50 and is continuously recirculated by a pump 52.

The cooling tubes 14 may be fashioned of any tubular structure which is electrically insulated from the applied electrical field. Cooling tubes 14 may be discrete from or integral with the planar body of each subcompartment 12. For example, cooling tubes 14 may be made of a plastic material which has a high dielectric strength to avoid electrical conduction to the coolant and has thin walls to facilitate high thermal transfer rates. Suitable plastic materials are tetrafluoroethylene or fluorinated ethylpropylene resins marketed under the trademark TEFLON or polypropylene co-polymers, polyethelyene or silicone. Alternatively, the cooling tubes 14 may be made of a ceramic or glass having high thermal transfer properties, and the glass or ceramic tubes may have metalization layers on luminal surfaces thereof, which is thereby electrically isolated from the electric field and which facilitates heat transfer to the cooling medium. Similarly, cooling tubes 14 which are integral with the planar body of each subcompartment 12 may consist of chambers within each planar body for circulating a coolant medium therethrough, or may consist of inter-subcompartmental channels formed in the planar surface of each planar body and which reside between adjacent subcompartments 12. Regardless of the configuration of the cooling tubes 14, they must be in thermal communication with the separation channel 16 and capable of conducting Joule heat away from the separation channel 16.

Cooling tubes 14 may have any suitable cross-sectional shape, but are preferably circular or quadrilateral. Cooling tubes 14 preferably have a cross-sectional dimension which corresponds to the thickness of the planar body forming the subcompartment 12, and, therefore, have substantially the same width or depth as that of the channel 16. Non-integral cooling tubes 14 may be affixed to the side walls of the channel 16 by gluing, welding, or other suitable method of affixation as may be known in the art, the cooling tubes may be molded directly into the material forming the planar body of the subcompartment 12, or the cooling tubes 14 may be extruded or otherwise formed as an integral part of the planar body of the subcompartment 12.

Sufficient cooling of the sample volume in the cavity is achieved only when the entire volume of the sample fluid is in close proximity to the surface area of the heat exchange means 14. It has been found preferable to have the sample fluid within a range of about 0.05 cm to about 0.15 cm away from any heat exchange means 14 surface to provide effective cooling of the sample fluid. Thus, the desirable width of channel 16, as measured by the lateral distance between the two parallel cooling tubes 14 is from about 0.1 cm to about 0.3 cm.

Providing internal cooling adjacent to the separation chamber permits use of a higher applied potential for the separation process which increases both the resolution and the speed of the separation. An advantage of the apparatus according to the present invention over designs of the prior art is the configuration of a long narrow separation chamber having internal cooling. As long as the ratio of cooling surface area to process volume remains constant or is increased, the device can be scaled to any sample cavity volume desired, simply by increasing the length and the number of subcompartments 12, without loss of resolution.

SECOND EMBODIMENT

Laterally Introduced Buffer Counterflow Gravity Biased Charge-Flow Separator

Figure 5A:
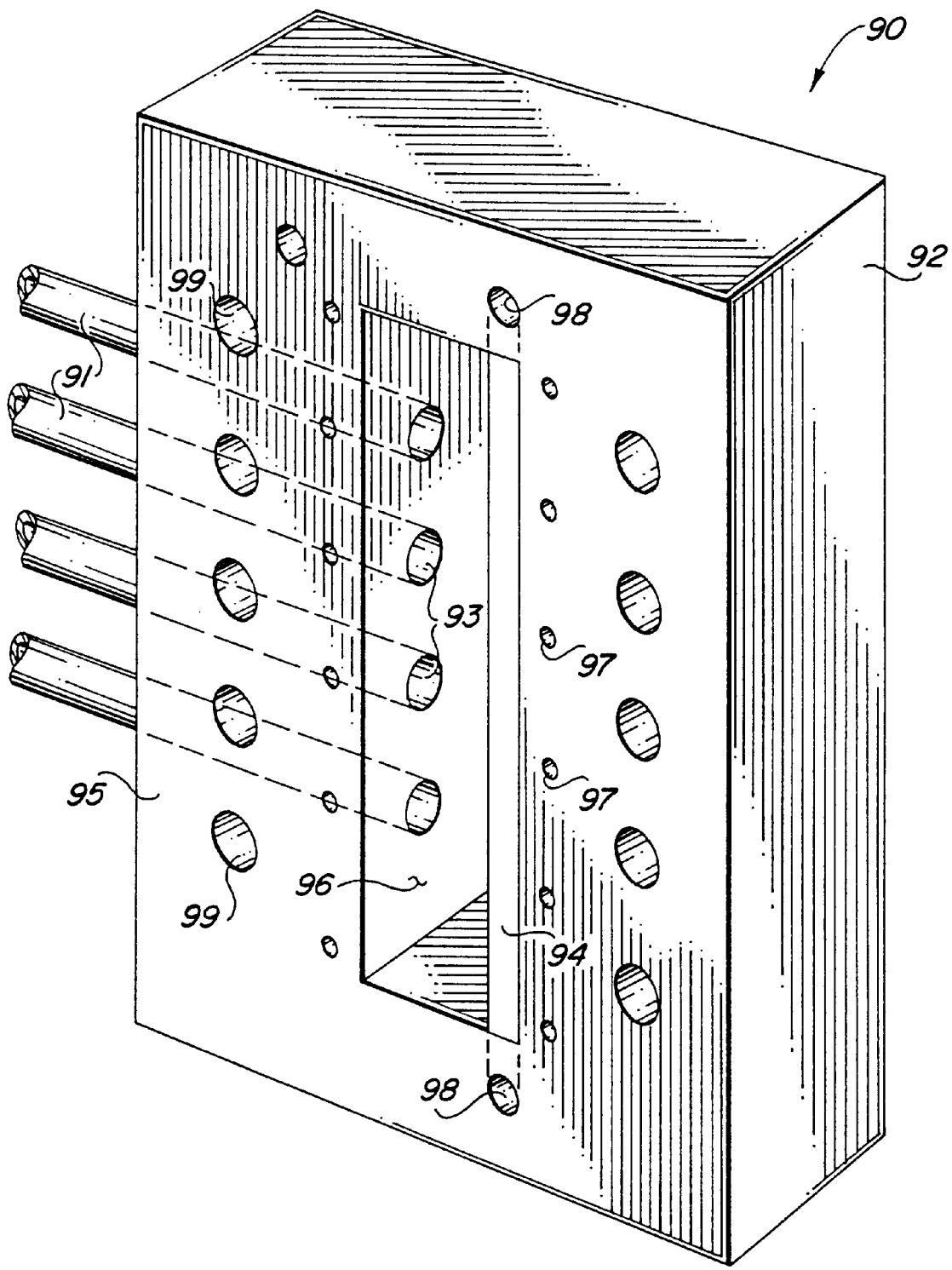
FIG. 5A is a perspective view of an end lateral buffer flow cell in accordance with a second embodiment of the charge-flow separation apparatus according to the present invention.

Turning now to FIGS. 5 and 5A, there is illustrated a second embodiment of a charge-flow separator apparatus 60 which employs a laterally introduced buffer counterflow and a gravity biased sample flow. The charge-flow separator apparatus 60 (CFS 60) is largely identical to that of the first embodiment of the charge-flow separator apparatus 10 (CFS 60), described above. Specifically, the CFS 60 includes a plurality of planar spacer members 62 formed in a parallel array, identified as 1–12 in FIG. 5, with screen members interdisposed therebetween (not shown) as described above with reference to the CFS 10. Each of the plurality of planar spacer members 62 are identical to those described above with reference to FIG. 3 and as described in U.S. Pat. Nos. 5,336,387 and 5,173,164, incorporated herein by reference Two planar end-spacer members 90, identified as 0 and 00 in FIG. 5, form end boundary fluid flow members for introduction and withdrawal of a buffer counterflow 75 through the parallel array of planar spacer members 62. Electrodes 61 and 64 form an anode and cathode, respectively, at opposing ends of the parallel array of planar spacer members 62 and the planar end-spacer members 90. Electrodes 61 and 64 are electrically connected to an appropriate variable power supply (now shown) to provide an electromotive force within the separation chamber. Each of the electrodes 61 and 64 are in fluid flow communication with an electrode buffer reservoir 70 and an electrode buffer pump 68 to recirculate an electrode buffer through the electrode compartments as hereinbefore described with reference to the CFS 10.

A throughput sample flow 63 is introduced into the parallel array of planar spacer members 62 from a sample container 58 under the influence of a throughput pump (T-Pump) 72. The T-Pump 72 is capable of introducing the throughput sample flow 63 into a first end of a selected one or more of the planar spacer members 62. A separated sample flow 65 is withdrawn from a second end of each of the planar spacer members 62 under the influence of a fraction pump (F-Pump) 73 which feeds the separated samples from each of the plurality of planar spacer members into a fraction collector 74. The operational parameters of sample flow 63 and separated sample flow 65, T-Pump 72, F-Pump 73, and fraction collector 74 are more full set forth above with reference to FIGS. 1–4 and in U.S. Pat. Nos. 5,336,387 and 5,173,164, incorporated herein by reference.

Two significant areas of difference exist between CFS 60 and CFS 10. The first of these differences results from the CFS 60 being oriented such that sample inflow 63 occurs at the bottom each of a plurality of separation chambers 62 and separated sample outflow 65 occurs at the top of each of the plurality of separation chambers 62. In this manner, the sample flow through the plurality of separation chambers 62 is biased against ambient gravity 85. Biasing the sample flow through the plurality of separation chambers 62 reduces zone sedimentation effects on cell populations normally found in sample flows which are normal to the gravity vector 85. By reducing the zone sedimentation effect on the cell populations, the gravity biasing of the present invention effectively increases throughput with correspondingly longer residence times in the separation chamber.

The second of these differences is a lateral orientation of the buffer fluid flow 77 and 79. As best illustrated in FIG. 5A, the lateral buffer fluid flow 77 and 79 is facilitated by modification of the spacer members 12 described above with reference to FIG. 3. Turning to FIG. 5A, a generally rectilinear planar end-spacer member 90 is provided with a fluid flow opening 96 longitudinally oriented therein. The fluid flow opening 96 is bounded on an upper, a lower and lateral surfaces thereof by the spacer member 90, but is open to frontal and rearward planar surfaces of the planar end-spacer member 90. A cooling member 94, similar to the cooling member 14 described above with reference to the CFS 10 is disposed along one lateral surface of the fluid flow opening 96 forming one lateral boundary of the fluid flow opening. The cooling member 94 is connected, in fluid flow communication with inlet and outlet ports 98 also disposed in the planar end-spacer member 90. Inlet and outlet ports 98, in turn, communicate with an external fluid cooling medium and heat exchanger (not shown, but identical to that of the CFS 10, heretofore described).

A plurality of buffer ports 93 are disposed on a second lateral surface of the fluid flow opening 96, which open into the fluid opening 96 in the direction of and opposite to the cooling member 94. Each of the plurality of buffer ports 93 are connected, through a first lateral wall 95 of the planar end-spacer member 90, to a plurality of tubular members 91. Tubular members 91 serve either to convey a buffer fluid flow 77 from an external buffer reservoir 80 to the plurality of buffer ports 93 under the influence of a multichannel counterflow buffer pump (C-Pump) 76 or from the plurality of buffer ports 93 to either a second fraction collector or to waste 82 under the influence of a second multichannel fraction pump (F-Pump') 78. Thus planar end-spacer 0 serves to receive the buffer inlet flow 77 from the C-Pump 76, while planar end-spacer 00 serves to convey the buffer outlet flow 79 to either fraction collector or waste 82 under the influence of F-Pump' 78, thereby creating the buffer counterflow 75 across the parallel array of planar spacer members 62 in a direction opposing the applied electrical field 71.

The buffer inlet flow 77 and the buffer outlet flow 79 are, therefore, laterally oriented relative to the planar end-spacer member 90 used as the buffer inlet member and the fluid opening 96 within the planar end-spacer member 90. By orienting the buffer ports 93 laterally relative to the planar end-spacer member 90, the buffer inlet flow 77 and the buffer outlet flow 79 are perpendicular to the axis of the buffer counterflow 75 through the plurality of planar spacer members 62 and the axis of the applied electrical field 71. In this manner a generally laminar buffer counterflow 75 through the plurality of planer spacer member 62 results.

It has been found that the CFS 60, described above, is especially well suited for enriching fetal NRBCs from maternal blood samples. Because the CFS 60 employs a horizontal crossflow fluid gradient 75 opposing the mobility induced by the applied electric field 71, cells flowing vertically accumulate into particular compartments when the electrophoretic mobility of the cells is countered by the buffer counterflow.

EXAMPLE I

Ten whole blood samples (10–40 ml in anticoagulant) were obtained from 9 pregnant women and one postpartum female by venipuncture. Cord blood specimens, adult male whole blood specimens and whole blood specimens from nulliparous women served as controls. The blood samples were layered on a Ficoll gradient and centrifuged. After centrifugation, the nucleated cell layer was removed, washed and re-suspended in buffer (triethanolamine, 10 mM; glycine, 280 mM; glucose, 11 mM, acetic acid to pH 7.2). The re-suspended cells were processed through CFS 60 configured with 12 separation channels, 10 counterflow input channels and 4 counterflow output channels. The resuspended cells were introduced in an sample input flow, with the sample buffer input having a flow rate of 0.270 ml/min/channel, with a buffer output flow rate of 0.220 ml/min/channel and a counterflow rate of 1.8 ml/min, in the presence of an applied electric field of 250 V at 68–72 mA.

After processing, the fetal NRBCs were collected and identified histologically after staining with Giesma and benzidine to stain the nuclei blue and the cytoplasm brown. The cells were enumerated at 400× under light microscopy in a grid reticule of 0.06 $mm^2$. A Hettich cytocentrifuge was used to prepare slides.

In each case, 1–7 NRBC's per 1000 maternal cells were counted, with a mean of 3.8±1.75 (SD) cells. Among 5 cases, 265–1430 NRBCs per slide were counted, with a mean of 531.6±504.2 (SD) cells. These cells were present in the blood of the pregnant and postpartum females and cord blood, but were not found in the control adult males or nulliparous females. There does not appear to be a correlation between gestational age and the frequency of NRBCs in maternal blood. The data are summarized in Table 1, below:

TABLE 1

| Case | Gestation (Weeks) | Fetal Sex | NRBC per 1000 WBC | NRBC per slide |
|---|---|---|---|---|
| 1 | 15.5 | XY | 7 | |
| 2 | 16.0 | NR | 5 | |
| 3 | 18.0 | NR | 3 | 265 |
| 4 | 20.0 | XY | 5 | |
| 5 | 20.5 | XY | 3 | 321 |
| 6 | 21.5 | XY | 2 | 1430 |
| 7 | 24 | NR | 3 | |
| 8 | 26 | XY | 1 | 374 |
| 9 | 28 | XY | 4 | |
| 10 | 30.5 | XY | 5 | 268 |

EXAMPLE II

Whole blood samples were obtained on anticoagulant from 6 females by venipuncture and separated in a charge-flow separator under conditions identical to those in Example I above. Separated samples were obtained from the charge-flow separator and processed as described in Example I. Table II summarizes the results:

TABLE II

| Case | Gestation (Weeks) | No. NRBCs/WBC in Peak Fraction |
|---|---|---|
| A-11 | 11 | 7/993 |
| A-13 | 12 | 5/995 |
| A-8 | 15.5 | 67/993 |
| A-6 | 24 | 3/997 |
| A-5 | 9.0 | 12/988 |
| A-9 | 12.0 | 8/992 |

EXAMPLE III

Whole blood samples were collected on anticoagulant from 3 pregnant women by venipuncture. The blood samples were processed by charge-flow separation in the buffer described in Example I, operated under the following conditions: the sample buffer input having a flow rate of 0.220 ml/min/channel, with a buffer output flow rate of 0.270 ml/min/channel and a counterflow input rate of 4.04 ml/min and a counterflow output flow rate of 1.48 ml/min, in the presence of an applied electric field of 325 V at 90–100 mA. To achieve T-Pump rate less than the F-Pump rate, in conjunction with a differential counterflow in and counterflow out rate, a counterflow buffer inflow line was added from the C-Pump into the bottom of buffer inflow spacer 0, and a counterflow buffer outflow line was added from the top of buffer outflow spacer 00 to the Fpump' 78 as indicated in phantom on FIG. 5.

The results of this separation are detailed in Table III, below:

TABLE III

| Case | Gestation (Wks) | No. NRBCs/WBC in Peak Fraction |
|---|---|---|
| A-24 | 7.5 | 55/945 |
| A-25 | 12.0 | 3/997 |
| A-27 | 20.5 | 3/997 |

Alternative operating conditions may be employed, such as different buffers, different separation times, different fluid flow rates, different voltage and wattage have been found useful while realizing enrichment of the fetal NRBCs from a maternal whole blood sample. For example, a buffer consisting of 5 mM triethanolamine, 22 mM glucose, 280 mM glycine and acetic acid to pH 7.33 has been used in a CFS 60 in which the sample input flow rate was 0.22 ml/min/channel, the sample output flow was 0.37 ml/min/channel and the crossflow pump was operated at 3.75 ml/min, in the presence of an electrical field generated at 325 volts and 55 mA, with comparable enrichment of fetal NRBCs as found in the examples stated above.

The foregoing examples should be understood to be merely as non-limiting examples of the operation of the charge-flow sepration system and method of separating fetal nucleated red blood cells from a maternal blood sample. Those skilled in the art will understand and appreciate, that other operational parameters, including flow rates, applied voltage, buffer constitutions or pre-processing methods for separating nucleated from enucleated cells in a whole blood samples may be employed without departing from the spirit and scope of the present invention.

It has been found that the mobility of fetal NRBCs in an electric field is intermediate between the fastest enucleated red blood cells and the slowest white blood cells. Thus, for example, where enucleated red blood cells elute in fractions 4–7, and leukocytes elute from fractions 6–8, it has been found that the nucleated fetal red blood cells elute in fractions 6–8 with the peak in fraction 7. The CFS 60 is well suited to run in a tandem or in-series mode in which a first run is conducted to conduct a gross separation as noted above, and the fractions of interest, e.g., fractions 6–8, which contain the peak nucleated fetal red blood cells, but also the fastest enucleated red blood cells and the slowest leukocytes, can be conducted to a second CFS 60 set to run at voltage, wattage, T-Pump, F-Pump, and C-Pump flow rates which are set different from the first run CFS in order to amplify the 3 fraction sample across a larger number of channels, e.g., 10–12. This second, or tandem, CFS 60 run then provides a finer separation of the fetal NRBCs than that obtained from the first run.

THIRD EMBODIMENT

Adsorption-Filtration and Affinity Matrix Charge-Flow Separation

Turning now to FIGS. 6–9, there is disclosed the use of at least one leukocyte-depleting matrix which preferentially captures leukocytes by at least one of adsorption, filtration and affinity as described in U.S. Pat. No. 4,925,572 or PCT Publication No. WO 94/17209, incorporated herein by reference. The preferable leukocyte-depleting matrices are "LEUKOSORB A" and "LEUKOSORB B" both manufactured and sold by Pall Corporation. For purposes of illustration only, the leukocyte-depleting matrices depicted in FIGS. 6–9 are identified by LEUKOSORB A and LEUKOSORB B, but any type of adsorption, filtration or affinity matrix which functions to preferentially pass nucleated red blood cells or white blood cells and red blood cells in a manner as described in FIGS. 6–9 is contemplated as being useful.

Figure 6:
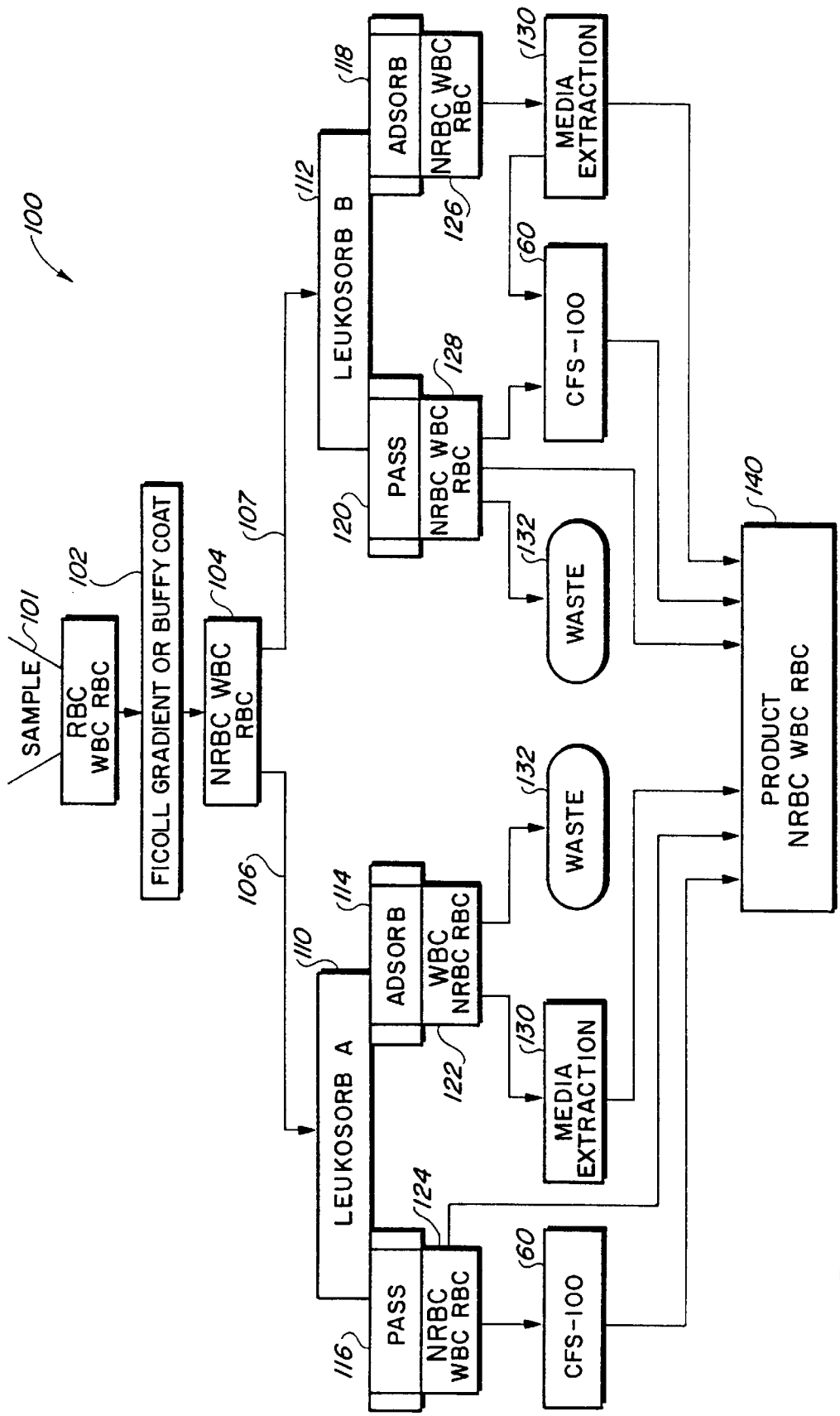
FIG. 6 is a flow diagram illustrating a first embodiment of the adsorption-filtration separation method of the present invention.

FIG. 6 illustrates a first embodiment 100 of the absorption-filtration process in accordance with the present invention. A whole blood sample containing erythrocytes (RBC), leukocytes (WBC) and nucleated erythrocytes (NRBC) is layered onto a Ficoll gradient 102 as described earlier. Density gradient centrifugation on the Ficoll gradient separates a major fraction containing NRBC and WBC with few RBC components 104. The NRBC/WBC fraction is passed 106, 107 either over a LEUKOSORB A 110 or a LEUKOSORB B 112 adsorption-filtration medium. Passing the NRBC/WBC fraction 104 over the LEUKOSORB A 110 in step 106, passes 116 a fraction which includes a major fraction of NRBC 124 and an accompanying minor fraction of WBC and RBC, while a major fraction of WBC 122 and an accompanying minor fraction of NRBC and RBC 122 is adsorbed 114 on the LEUKOSORB A 110. Alternatively, in step 107, the NRBC/WBC fraction 104 may be passed over a LEUKOSORB B 112 medium, and a fraction of NRBC, WBC and RBC 128 is passed, while a major fraction of NRBC and WBC 126, with an accompanying minor fraction of RBC is adsorbed.

The NRBC fraction 124 from step 106 is then passed through the CFS 60, described above, to further concentrate the desired rare cell population product 140. Further, the adsorbed fraction 130 may be extracted 130 by desorbing with an extraction medium appropriate for the adsorbed cell population to yield the desired cell population product 140.

Alternatively, if step 107 is followed, the fraction 128 passing through the LEUKOSORB 112 is either discarded as waste 132 or is concentrated by CFS 60, as described above. The adsorbed fraction 126 may be desorbed 130 to yield the desired cell population product 140, or concentrated by CFS 60, as described above, to yield the desired cell population product 140.

It is to be noted that in the FIGS. 6–9, major fractions are denoted by larger typeface legends and minor fractions are denoted by smaller typeface legends. Thus, for example, in FIG. 6, the whole blood sample 100 contains a major fraction of erythrocytes (RBC) and minor fractions of leukocytes (WBC) and nucleated erythrocytes (NRBC). After the density gradient centrifugation at step 102, the fraction containing a major fraction of nucleated erythrocytes (NRBC) and leukocytes (WBC) and a minor fraction of erythrocytes (RBC) is recovered. Thus, density gradient centrifugation removes a major fraction of erythrocytes and passes the minor fraction of WBC and NRBC.

Figure 7:
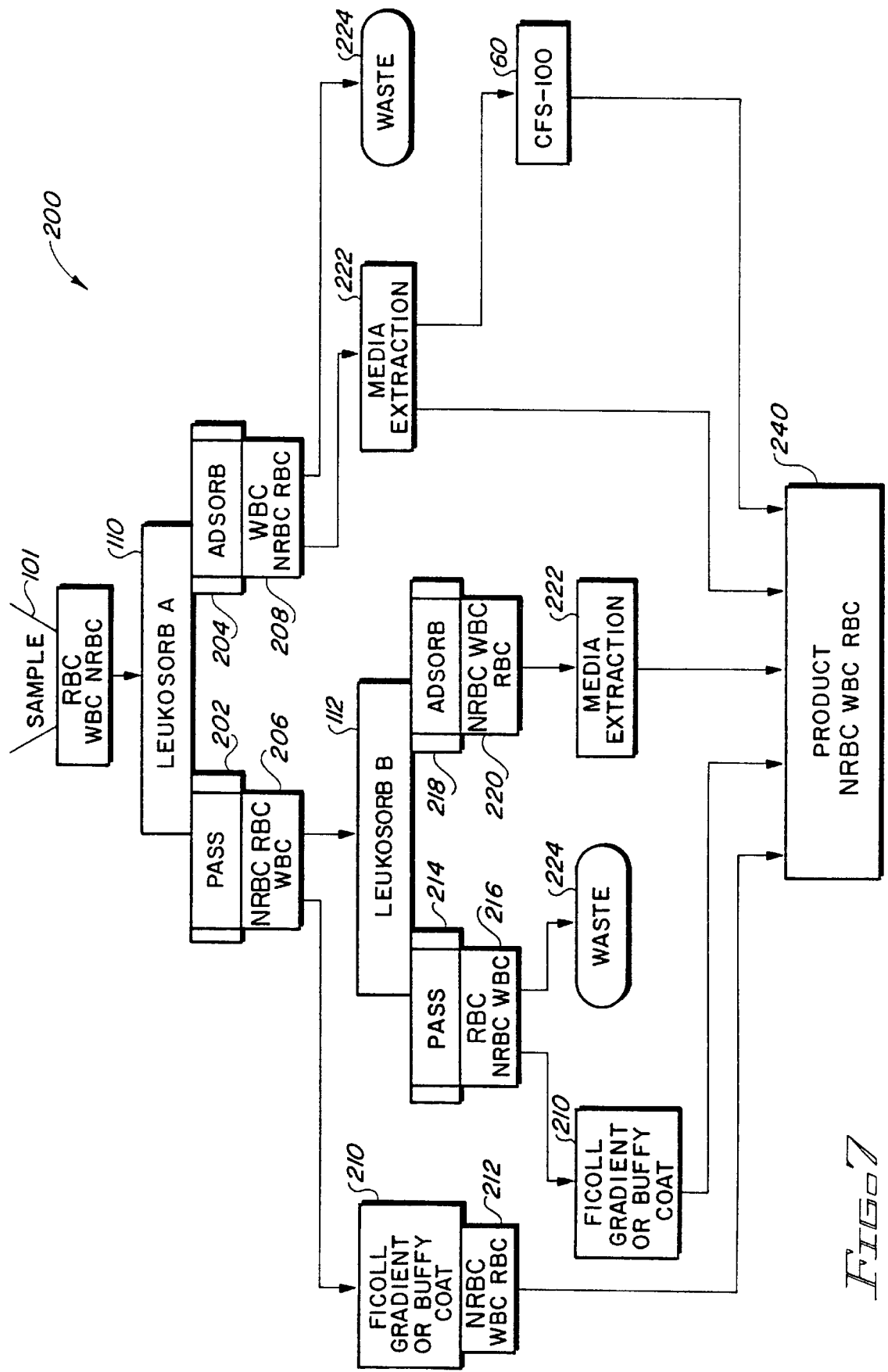
FIG. 7 is a flow diagram illustrating a second embodiment of the adsorption-filtration separation method of the present invention.
Figure 8:
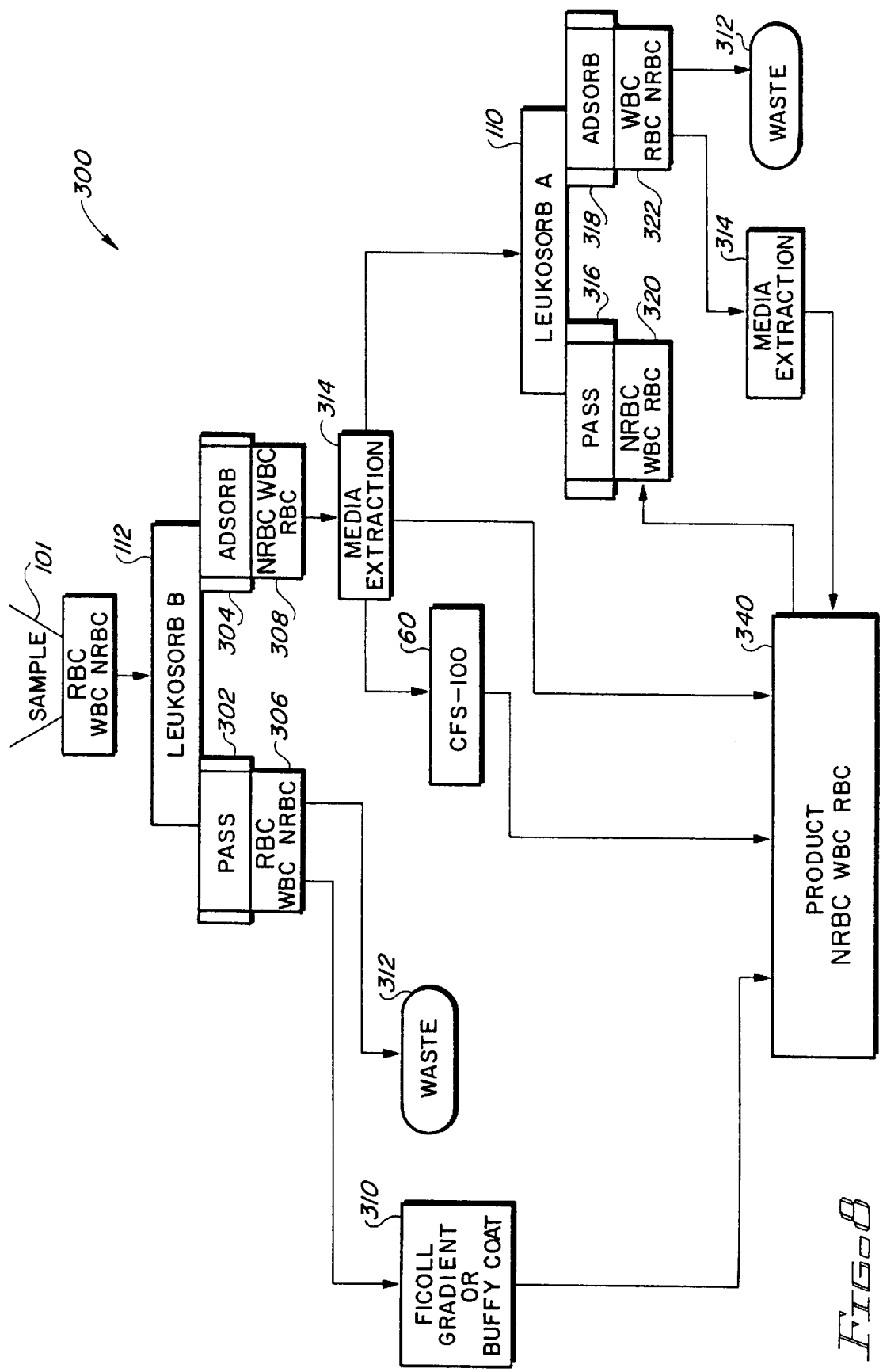
FIG. 8 is a flow diagram illustrating a third embodiment of the adsorption-filtration separation method of the present invention.
Figure 9:
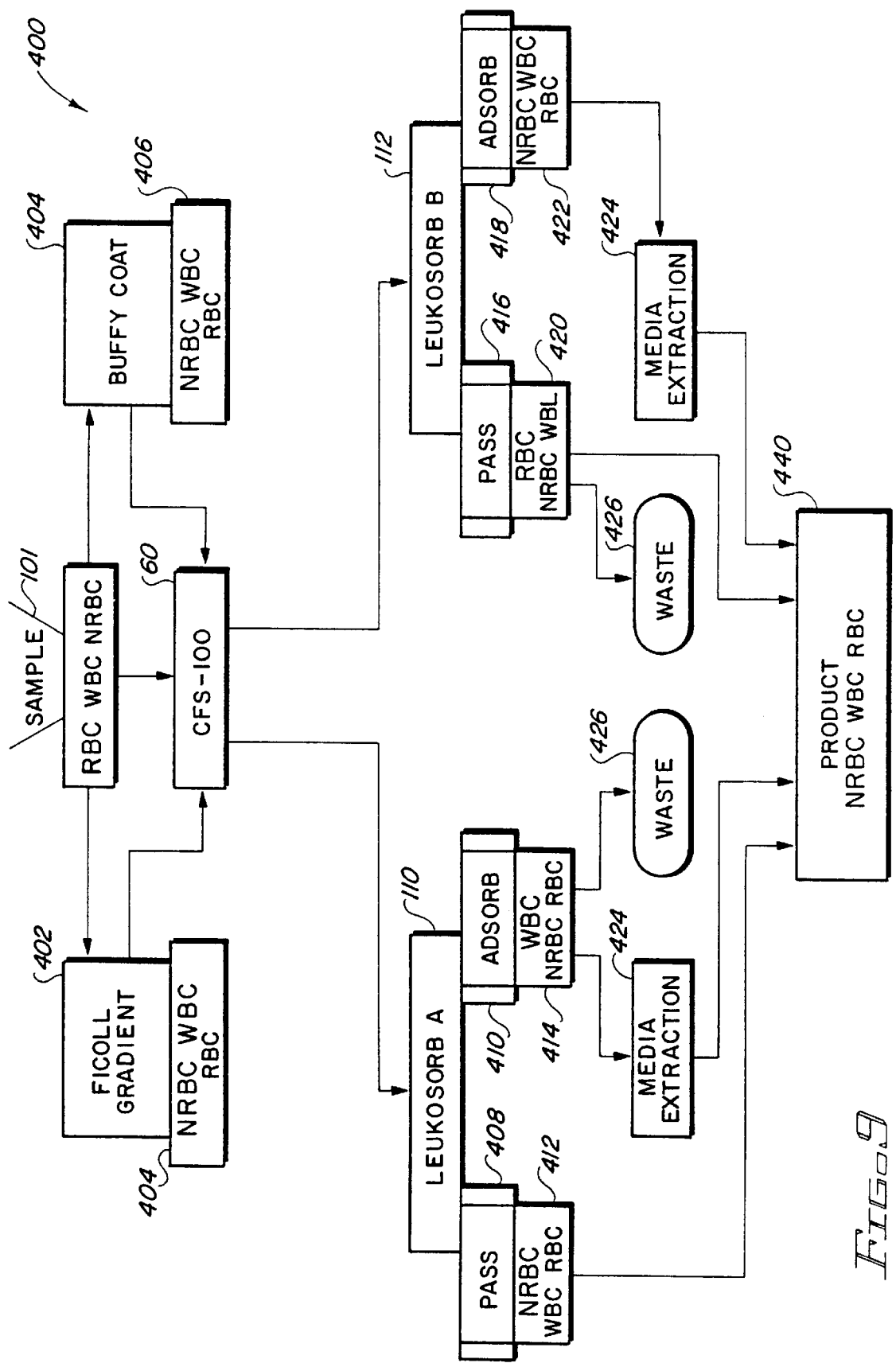
FIG. 9 is a flow diagram illustrating a fourth embodiment of the adsorption-filtration separation method of the present invention operated in conjunction with the charge-flow separation method of the present invention.

FIGS. 7–9, set forth a second embodiment of the adsorption-filtration process 200, a third embodiment of the adsorption-filtration process 300, and a fourth embodiment of the adsorption-filtration process 400, respectively. In each of embodiment 200, 300 and 400, the basic process steps are identical, except that the order of performing the process steps has been altered between the embodiments as illustrated in the Figures. For example, in FIG. 7, the sample is placed onto a LEUKOSORB A medium 110, then passed either to a Ficoll gradient for density gradient centrifugation and separation of the desired cell population, or the fraction passing is placed onto a LEUKOSORB B medium 112, and the fraction passing is subject to density gradient centrifugation 210 to yield the product 240. The adsorbed fraction on the LEUKOSORB B medium 112, is extracted 222 to yield the desired product 240. The fraction adsorbed on the LEUKOSORB A medium 110 is extracted 222, and may be concentrated by CFS 60, to yield the desired cell population 240.

In FIG. 8, the sample is placed onto a LEUKOSORB B medium 112, the fraction passed is subjected to density gradient centrifugation 310 or is waste 312, while the adsorbed fraction 304 is extracted 314 and subjected to CFS 60 to yield the product 340, or the extracted fraction is passed onto LEUKOSORB A medium 100 for further adsorption 318 or filtration 316 to either positively or negatively select the desired product 340.

Finally, in FIG. 9, the sample either first subjected to CFS 60, or is subjected to density gradient centrifugation 404 followed by CFS 60. The concentrated sample from CFS 60, is then passed onto either LEUKOSORB A medium 110 and LEUKOSORB B medium 112, each either positively (passing) or negatively (adsorbing) the desired cell population 440.

The adsorption-filtration affinity method of the present invention entails layering a maternal blood sample onto a fibrous adsorption-filtration filter medium having a nominal pore size of about 8 microns and being capable of 40–80% leukocyte immobilization, with a 70–80% post-wash leukocyte retention rate, and which is extremely hydrophilic, being capable of wetting with solutions having surface tensions of up to 85–90 dynes, which has a hold up volume of 40–70 $\mu$l/cm$^2$ for a single layer of adsorption-filtration filter medium and which is characterized by low to medium protein binding. The preferred adsorption-filtration separation filter medium is that sold by Pall Corporation under the trademarks "LEUKOSORB" TYPES A and B or that described in U.S. Pat. Nos. 4,923,620, 4,925,572, or European Patent No. 313348, each of which is hereby incorporated by reference.

Those skilled in the art will appreciate, from the foregoing, that while the present invention has been described with reference to its preferred embodiments, that the spirit and scope of the present invention is not intended to be limited thereto, but by the claims appended hereto.

What is claims:

1. Apparatus for separating nucleated blood cells from a blood sample, comprising:

at least one of a plurality of vertically oriented separation chambers, each of said separation chambers being defined by lateral side walls, lower fluid flow ports for introducing a blood sample therethrough, upper fluid flow ports for collecting a treated blood sample therefrom and frontal and rearward openings for accommodating a buffer fluid flow and mobility of blood cells therethrough;

thermal transfer means for conducting heat from fluid within the at least one of a plurality of vertically oriented separation chambers, said thermal transfer means being in thermal communication with the lateral side walls of the at least one of a plurality of vertically oriented separation chambers;

a buffer inflow spacer member adjacent a first of the at least one of a plurality of vertically oriented separation chambers, said buffer inflow spacer member having a buffer inflow slot in fluid flow communication with an entire area of the first of the at least one of a plurality of vertically oriented separation chambers and having a plurality of buffer inflow ports laterally disposed in said buffer inflow spacer member such that a flow of buffer into said buffer inflow spacer member through said plurality of buffer inflow ports is introduced into said buffer inflow slot and passes through said buffer inflow slot as a substantially laminar fluid flow;

a buffer outflow spacer member adjacent a second of the at least one of a plurality of vertically oriented separation chambers, said buffer outflow spacer member having a buffer outflow slot in fluid flow communication with an entire area of the second of the at least one of a plurality of vertically oriented separation chambers and having a plurality of buffer outflow ports laterally disposed in said buffer outflow spacer member such that a flow of buffer from said buffer outflow spacer member and said plurality of buffer outflow ports passes through said buffer outflow slot as a substantially laminar fluid flow;

first pumping means for introducing a flow of a blood sample into the at least one of a plurality of vertically oriented separation chambers through said lower fluid flow port, such that said flow of a blood sample is gravity biased;

at least a pair of electrodes for imparting an electrical field across the at least one of a plurality of vertically oriented separation chambers; and second pumping means for introducing a flow of a buffer fluid across the at least one of a plurality of vertically oriented separation chambers in a direction substantially opposing a direction of cellular mobility in the imparted electric field.

2. The apparatus of claim 1 wherein said thermal transfer means comprises at least one cooling member disposed along one lateral surface of a fluid flow opening of said buffer outflow spacer member.

3. The apparatus of claim 2 wherein the cooling member is connected in fluid flow communication with an inlet and an outlet disposed in the buffer outflow spacer member, said inlet and outlet communicating with external cooling means.

4. The apparatus of claim 3 wherein said buffer inflow ports are disposed on a second lateral surface of the fluid flow opening opposite to the cooling member, said buffer inflow ports connected to a plurality of tubular members.

5. The apparatus of claim 1 further comprising a third pumping means for conveying the buffer fluid either to one of fraction collection means and waste collection means.

6. The apparatus of claim 1 further comprising screen members interdisposed between said plurality of vertically oriented separation chambers.

* * * * *